United States Patent [19]

Smith

[11] Patent Number: 4,480,144
[45] Date of Patent: Oct. 30, 1984

[54] REGENERATION OF AROMATICS PROCESSING CATALYSTS

[75] Inventor: Fritz A. Smith, Rye, N.Y.

[73] Assignee: Mobil Oil Corporation, New York, N.Y.

[21] Appl. No.: 290,644

[22] Filed: Aug. 6, 1981

[51] Int. Cl.³ .............................................. C07C 5/24
[52] U.S. Cl. ..................................... 585/481; 502/51; 502/52
[58] Field of Search ................ 585/481; 252/416, 419; 502/51, 52

[56] References Cited

U.S. PATENT DOCUMENTS

| | | | |
|---|---|---|---|
| 2,225,402 | 12/1940 | Liedholm | 502/52 |
| 2,391,327 | 12/1945 | Mekler | 502/52 |
| 3,041,290 | 6/1962 | Porter et al. | 502/52 |
| 3,649,559 | 3/1972 | Cooper | 502/52 |
| 3,756,961 | 9/1973 | Francis et al. | 502/52 |
| 4,236,596 | 12/1980 | Tabak et al. | 502/52 |
| 4,300,014 | 11/1981 | Yamasaki et al. | 502/52 |

Primary Examiner—Delbert E. Gantz
Assistant Examiner—A. Pal
Attorney, Agent, or Firm—A. J. McKillop; M. G. Gilman; L. G. Wise

[57] ABSTRACT

Regeneration of an aromatics processing catalyst is effected in the absence of a gas cooler and a gas-liquid separator with a continuous loop flow of an oxidizing gas stream by removing a portion of said continuous closed loop flow and introducing therein a quantity of a low moisture content molecular oxygen containing gas effective to maintain a molecular oxygen content no greater than 1.0 mole percent and a water partial pressure no greater than about 1.0 psi.

20 Claims, 2 Drawing Figures

REGENERATION OF AROMATICS PROCESSING CATALYSTS

BACKGROUND OF THE INVENTION

1. Field of the Invention

This invention relates to improvements in the conversion of aromatics. More particularly, it relates to the regeneration of aromatics processing catalysts. This invention especially relates to the regeneration of zeolite catalysts employed in aromatics conversions.

2. Background of the Invention

The prior art is replete with processes relating to the manufacture of aromatic compounds having six to eight carbon atoms, namely benzene, toluene and xylene (BTX). At the present time, the most valuable of these is p-xylene, which may be separated for use in synthesis of polyesters from mixed xylenes by fractional crystallization or by selective adsorption. Also highly valued is benzene for use as chemical raw material. Toluene is also valuable for varied uses as a solvent in chemical manufacture and as a high octane gasoline component.

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|  | Freezing Point °F. | Boiling Point °F. | Density Lbs./ U.S. Gal. |
|---|---|---|---|
| Ethylbenzene | −139.0 | 277.0 | 7.26 |
| P-xylene | 55.9 | 281.0 | 7.21 |
| M-xylene | −54.2 | 282.4 | 7.23 |
| O-xylene | −13.3 | 292.0 | 7.37 |

Principal sources are catalytically reformed naphthas and pyrolysis distillates. The $C_8$ aromatic fractions from these sources vary quite widely in composition but will usually be in the range 10 to 32 wt. % ethylbenzene with the balance, xylenes, being divided approximately 50 wt. % meta, and 25 wt. % each of para and ortho.

Individual isomer products may be separated from the naturally occurring mixtures by appropriate physical methods. Ethylbenzene may be separated by fractional distillation although this is a costly operation. Ortho-xylene may be separated by fractional distillation and is so produced commercially. Para-xylene is separated from the mixed isomers by fractional crystallization or by selective adsorption.

As commercial use of para and ortho-xylene has increased there has been interest in isomerizing the other $C_8$ aromatics toward an equilibrium mix and thus increasing yields of the desired xylenes. At present, several xylene isomerization processes are available and in commercial use.

The isomerization process operates in conjunction with the product xylene or xylenes separation process. A virgin $C_8$ aromatics mixture is fed to such a processing combination in which the residual isomers emerging from the product separation steps are then charged to the isomerizer unit and the effluent isomerizate $C_8$ aromatics are recycled to the product separation steps. The composition of isomerizer feed is then a function of the virgin $C_8$ aromatic feed, the product separation unit performance, and the isomerizer performance.

It will be apparent that separation techniques for recovery of one or more xylene isomers will not have material effect on the ethylbenzene introduced with charge to the recovery/isomerization "loop". That compound, normally present in eight carbon atom aromatic fractions, will accumulate in the loop unless excluded from the charge or converted by some reaction in the loop to products which are separable from xylenes by means tolerable in the loop. Ethylbenzene can be separated from the xylenes of boiling point near that of ethylbenzene by extremely expensive "superfractionation". This capital and operating expense cannot be tolerated in the loop where the high recycle rate would require an extremely large distillation unit for the purpose. It is a usual adjunct of low pressure, low temperature isomerization as a charge preparation facility in which ethylbenezene is separated from the virgin $C_8$ aromatic fraction before introduction to the loop.

Other isomerization processes operate at higher pressure and temperature, usually under hydrogen pressure in the presence of catalysts which convert ethylbenzene to products readily separated by relatively simple distillation in the loop, which distillation is needed in any event to separate by-products of xylene isomerization from the recycle stream. For example, the Octafining catalyst of platinum on a silica-alumina composite exhibits the dual functions of hydrogenation/dehydrogenation and isomerization.

In Octafining, ethylbenzene reacts through ethyl cyclohexane to dimethyl cyclohexanes which in turn equilibrate 5 to xylenes. Competing reactions are disproportionation of ethylbenzene to benzene and diethylbenzene, hydrocracking of ethylbenzene to ethane and benzene and hydrocracking of the alkyl cyclohexanes.

The rate of ethylbenzene approach to equilibrium concentration in a $C_8$ aromatic mixture is related to effective contact time. Hydrogen partial pressure has a very significant effect on ethylbenzene approach to equilibrium. Temperature change within the range of Octafining conditions (830° to 900° F.) has but a very small effect on ethylbenzene approach to equilibrium.

Concurrent loss of ethylbenzene to other molecular weight products relates to percent approach to equilibrium. Products formed from ethylbenzene include $C_6+$ naphthenes, benzene from cracking, benzene and $C_{10}$ aromatics from disproportionation, and total loss to other than $C_8$ molecular weight. $C_5$ and lighter hydrocarbon by-products are also formed.

The three xylenes isomerize much more selectively than the reaction of ethylbenzene, but they do exhibit different rates of isomerization and hence, with different feed composition situations the rates of approach to equilibrium vary considerably.

Loss of xylenes to other molecular weight products varies with contact time. By-products include naphthenes, toluene, $C_9$ aromatics and $C_5$ and lighter hydrocracking products.

Ethylbenzene has been found responsible for a relatively rapid decline in catalyst activity and this effect is proportional to its concentration in a $C_8$ aromatic feed mixture. It has been possible then to relate catalyst stability (or loss in activity) to feed composition (ethylbenzene content and hydrogen recycle ratio) so that for any $C_8$ aromatic feed, desired xylene products can be made with a selected suitably long catalyst use cycle.

A different approach to conversion of ethylbenzene is described in U.S. Pat. No. 3,856,872 of Morrison. Over an active acid catalyst comprising a crystalline zeolite characterized by a silica to alumina mole ratio of at least about 12 and a constraint index within the approximate range of 1 to 12, typically described as a ZSM-5 type zeolite, ethylbenzene disproportionates to benzene and diethylbenzene which are readily separated from xylenes by the distillation equipment needed in the loop to remove by-products. It is recognized that the rate of disproportionation of ethylbenzene is related to the rate of conversion of xylenes to other compounds, e.g. by disproportionation. See also U.S. Pat. No. 3,856,873 of Burress which also describes reaction of $C_8$ aromatics over ZSM-5 and shows effects of various temperatures up to 950° F. in the absence of metal co-catalyst and in the absence of hydrogen.

In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further advance in the art is described in U.S. Pat. No. 4,163,028 of Tabak, et al., which discloses xylene isomerization and ethylbenzene conversion at high temperature with ZSM-5 of very high silica/alumina ratio whereby the acid activity is reduced.

A more recent development of Tabak, et al., is found in U.S. Pat. No. 4,236,996 which discloses a low acidity zeolite catalyst, typified by ZSM-5, which has been steamed at high temperature to reduce its activity. In using this less active catalyst the temperature is raised to above 700° F. to attain xylene isomerization, preferably to 800° F. or higher. At these temperatures, ethylbenzene reacts primarily via dealkylation to benzene and ethane (or ethylene in the absence of hydrogen and hydrogenation co-catalyst) rather than via disproportionation to benzene and diethylbenzene and hence is strongly decoupled from the catalyst acid function. Since ethylbenzene conversion is less dependent on the acid function, a lower acidity catalyst can be used to perform the relatively easy xylene isomerization, and the amount of xylenes disproportionated is eliminated. The reduction of xylene losses is important because about 75% of the xylene stream is recycled in the loop resulting in an ultimate xylene loss of 6–10 Wt. % by previous processes. Since most of the ethylbenzene goes to benzene instead of benzene plus diethyl benzenes, the product quality of the new process is better than that of prior practices.

In addition to xylene isomerization, other aromatic conversion processes have gained importance. U.S. Pat. Nos. 3,126,422; 3,413,374; 3,598,878; 3,598,879 and 3,607,961 show vapor-phase disproportionation of toluene over various catalysts.

The disproportionation of aromatic hydrocarbons in the presence of zeolite catalysts has been described by Grandio et al. in the *Oil and Gas Journal*, Vol. 69, No. 48(1971).

The use of a catalyst comprising a crystalline zeolite characterized by a silica to alumina mole ratio of at least about 12 and a constraint index within the approximate range of 1 to 12 for the disproportionation of toluene is described in many patents, such as U.S. Pat. Nos. 4,011,276, 4,016,219, 4,052,476, 4,097,543, and 4,098,837. Other aromatic conversions such as transalkylation, cracking, alkylation and hydrocracking are typically conducted with this type of catalyst.

These catalytically promoted processes have a disadvantage found in many catalytic processes, catalyst activity declines due to deposition of "coke", a carbonaceous material, on the catalyst which progressively masks the active sites of the porous zeolite catalyst. The coke can usually be removed by burning with a molecular oxygen containing gas to regenerate the activity of the catalyst.

The regeneration of solid contact material of catalytic and non-catalytic nature contaminated with combustible deposits is taught in the prior art. U.S. Pat. No. 2,391,327 of Mekler discloses the regeneration of catalysts contaminated with heavy combustible materials with a cyclic flow. A regenerating gas stream passes through the contaminated catalyst, then through heat recovery and purifying equipment, through equipment where the free oxygen content, the temperature and other variables are adjusted to desired values and then back to the catalyst bed for further reactivation of the catalyst.

U.S. Pat. No. 3,755,961 of Francis et al. relates to the regeneration of coke-containing crystalline zeolite molecular sieves which have been employed in an absorptive hydrocarbon separation process. The process involves the continuous circulation of an inert gas containing a quantity of oxygen in a closed loop arrangement through the bed of molecular sieves. To prevent damage to the molecular sieve bed from water vapor, one of the combustion products of the regeneration, it is removed from the inert gas stream before the inert gas is recycled to the inlet to the molecular sieve bed. Commonly, the water vapor is removed by passage of the gas stream through a bed of water-lean water adsorbent. In addition, the circulatory gas stream is cooled by indirect heat exchange in an air or water cooled heat exchanger. Gas is vented from and inert gas and air are added to the circulating gas stream, as required.

Where catalyst activity declines rapidly, continuity of operation is achieved by the well-known "swing reactor" technique. In this procedure, two or more reactors are employed, one of which is on stream, while burning regeneration is conducted on a reactor containing spent catalyst which has lost activity by coke deposition. Cycles of two to four days or even less are common practice in this technique using one reactor on stream for that period and then shifting to a freshly regenerated vessel.

Longer operating times between regeneration are commercially desirable and have been attained in aromatic conversions. Cycles of several weeks or several months are not uncommon and operating runs as long as a year or more have been obtained. The use of specially prepared catalysts of controlled activity, the incorporation of metal into the zeolite catalyst and the addition of hydrogen to the reaction mixture have been some of the techniques employed in the prior art to obtain prolonged cycle times.

It has been taught heretofore that steam and high temperature like those encountered during regeneration to burn off coke were detrimental to zeolite structure and catalytic activity. The prior art aromatic processes taught the use of recycle gas driers to minimize exposure of the zeolite containing catalyst to water vapor formed during regeneration.

In direct contradiction to these prior art teachings, recycle gas driers are expressly not utilized in the regeneration process disclosed in commonly assigned patent application Ser. No. 121,340, filed Feb. 14, 1980. In this application, a catalyst comprising zeolite, which has a silica to alumina mole ratio of at least about 12 and a constraint index within the approximate range of 1 to 12, is regenerated in the presence of steam at water partial pressures of between about 0.1 psi and about 4.0 psi, at a contact time of between about 12 and about 72 hours and a temperature of between about 750° and about 900° F. The catalyst regenerated in this fashion can have an activity enhanced many times greater than its original activity which can be translated to longer cycle times. The regeneration process of said application controls the regeneration conditions to mildly steam the catalysts so as to enhance their activity, rather than to deactivate them. Oxidizing gas is passed to the reactor containing the bed of coked catalyst where it reacts with the coke to form a hot combustion gas stream. This hot gas stream is removed from the reactor, passed to a condenser and then to a separator operated at a temperature of about 35°–150° F. where liquid effluent is removed. The cooled gaseous stream containing water vapor is then introduced to a heater together with the required quantity of make-up oxidizing gas and the heated gas stream is recycled to the reactor for further regeneration of the catalyst.

It is an object of this invention to provide an improved process for regenerating an aromatics conversion catalyst comprising a zeolite.

It is another object of this invention to regenerate an aromatics conversion catalyst without employing a gas cooler and a gas-liquid separator.

It is a further object of the invention to regenerate a ZSM-5 type zeolite xylene isomerization catalyst of controlled low acid activity.

SUMMARY OF THE INVENTION

The above and other objects have been achieved by a catalyst regeneration process which maintains the water partial pressure and molecular oxygen contents of the regenerating gas at the desired low levels at the inlet to the catalyst bed by removing a quantity of the circulating regenerating gas and replacing it with quantities of low moisture content molecular oxygen containing gas. More particularly, the reduction in the activity of a zeolite-containing aromatics conversion catalyst may be minimized during oxidative regeneration by maintaining the oxygen and moisture contents of the circulating regenerating gas at low values by removing some of the regenerating gas and replacing it with an appropriate mixture of low moisture content air and nitrogen.

The present invention is directed to an improvement in a process for the conversion of aromatic containing feedstocks in which said feedstock is contacted in a reactor vessel, under conversion conditions, with a catalyst comprising a zeolite having a silica to alumina mole ratio of at least 12 and a constraint index within the approximate range of 1 to 12, and which includes a regeneration step to burn off carbonaceous materials which deposit on said catalyst, said regeneration step comprising contacting said catalyst containing carbonaceous materials with a continuous closed loop flow of a gas stream comprising oxidizing gas and steam at regeneration conditions including a steam partial pressure of between about 0.1 psi and about 4.0 psi, a contact time of between about 12 hours and about 72 hours and a temperature of between about 700° F. and about 1000° F., said improvement comprising:
(a) removing from said continuous closed loop flow a portion of said gas stream, and
(b) introducing into said continuous closed loop flow a quantity of a low moisture content molecular oxygen containing gas, said portion and said quantity being effective, collectively, to maintain, in the closed loop flow at the inlet to said reactor vessel, a molecular oxygen content no greater than about 1.0 mole percent and a water partial pressure no greater than about 1.0 psi.

In a preferred embodiment the present invention is directed to an improvement in a process for isomerizing the xylene content of a charge mixture of eight carbon atom aromatic hydrocarbon compounds which mixture contains xylene and ethylbenzene by contact at conversion conditions including a temperature of about 700° to about 1000° F. with a catalyst comprising a zeolite having a silica/alumina ratio greater than 12 and a constraint index of 1 to 12, said zeolite having been steamed prior to said contact under temperature and pressure conditions and a period of time such that the steamed zeolite requires an increased reaction temperature of at least 50° F. to equal the ethylbenzene conversion by the unsteamed zeolite and regenerating said catalyst to burn off carbonaceous materials which deposit on said catalyst by contacting said catalyst containing carbonaceous materials with a continuous closed loop flow of a gas stream comprising molecular-oxygen containing gas under regeneration conditions comprising a water partial pressure of between about 0.1 and about 1.0 psi, a contact time of between about 12 and about 120 hours and a temperature of between about 700° and about 925° F., said improvement in the regeneration comprising
(a) removing from said continuous closed loop flow a portion of said gas stream, and
(b) introducing into said continuous closed loop flow a quantity of a low moisture content, molecular-oxygen containing gas, said portion and said quantity being effective, collectively, to maintain, in the closed loop flow at the inlet to said reactor vessel, a molecular oxygen content no greater than about 1.0 mole percent and a water partial pressure no greater than about 1.0 psi.

DESCRIPTION OF THE PREFERRED EMBODIMENTS

Figure 1:
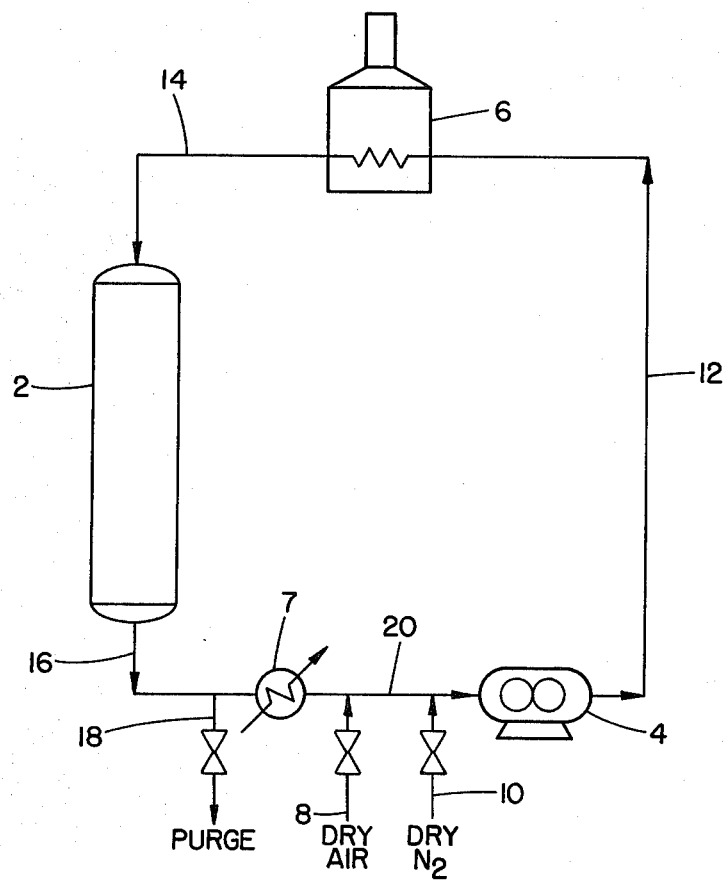
FIG. 1 is a flowplan of an embodiment of the process of the invention.

In accordance with the present invention, the regeneration of an aromatic conversion catalyst comprising zeolites is improved. The zeolites of concern herein are characterized by a silica to alumina mole ratio of at least about 12 and a constraint index within the approximate range of 1 to 12. These zeolites are referred to collectively herein as ZSM-5 type zeolites.

The present improvements reside in regenerating said zeolite catalysts with a molecular oxygen containing gas, such as air, and in the presence of steam under controlled conditions. The prior art has taught that steam and high temperature like those encountered during regeneration to burn off coke were detrimental to zeolite structure and catalytic activity. Recycle gas driers were therefore employed to minimize exposure of the zeolite catalyst. More recently, zeolite catalyst regeneration in the presence of steam under controlled conditions has been found advantageous in enhancing catalyst activity. In this latter regeneration process, recycle gas driers are expressly not utilized but limited steaming is achieved through the use of a recycle gas condenser followed by a gas-liquid separator operated at a temperature of about 35° to about 150° F. so as to maintain the partial pressure of water of the gas in contact with the catalyst at about 0.1 to about 4.0 psi.

It has been found, and this is the essence of this invention, that neither recycle gas driers nor the combination of a condenser and a gas-liquid separator are required to maintain a low water partial pressure in the circulating regeneration gas stream when regenerating an aromatic conversion zeolite catalyst. By withdrawing a quantity of the recycle gas after it exits from the reactor vessel and replacing this quantity with a low moisture content mixture of molecular oxygen and inert gas, such as air or nitrogen, the water partial pressure and the oxygen content can be maintained at effective levels to cause regeneration of the zeolite catalyst without substantial change in the level of catalytic activity.

The molecular oxygen containing gas employed in the process of this invention may be pure oxygen or a mixture of molecular oxygen with an inert gas. As used herein an inert gas is one which essentially does not react chemically with the catalyst composition during the regeneration. Therefore such "inert" gases as nitrogen, helium, carbon dioxide and the like may be employed. Since air contains both oxygen and an inert gas, it may be used herein. However, to obtain the desired result an additional supply of either oxygen or nitrogen will usually be required where air is being utilized as the principal source of oxygen. Therefore, mixtures of pure oxygen and nitrogen, air and nitrogen, air and carbon dioxide and the like may be employed in the practice of this invention.

It has been found that a convenient means of practicing this invention is to provide a controllable source of air and a controllable source of nitrogen to the process.

The water content of the molecular oxygen containing gas must be sufficiently lower than that of the circulating regeneration gas stream as said gas stream exits the catalyst bed so as to reduce the water content of the regeneration gas stream to no greater than about 1.0 psi at the inlet of the catalyst bed when a fresh quantity of the molecular oxygen containing gas is exchanged for a quantity of the recycle gas stream. It has been found that the dew point of the gas added to the recycle loop should be less than about $-15°$ F., preferably less than about $-40°$ F. and most preferably about $-60°$ F. When two sources of gas are utilized to provide the oxygen containing gas to the improved process of this invention, the dew point of the individual streams need not be within the above requirements provided that the dew point of the combined addition is within these dew point limitations. Ideally, and for simplicity of operation, the dew point of the several gas sources can be the same.

In a preferred embodiment of this invention, the catalyst being regenerated is a steamed ZSM-5 type zeolite which is being employed in xylene isomerization in accordance with U.S. Pat. No. 4,236,996. With this catalyst, it has been found that the improvements of this invention may be practiced under operating conditions which include a water partial pressure of between about 0.1 and about 1.0 psi, a contact time of between about 12 and about 120 hours and a temperature of between about 700° and about 925° F.

Regeneration of the aromatics processing catalyst is generally conducted in two steps, a main burn and a clean-up burn. The improvements of the invention are particularly directed to the main burn portion of the regeneration. The main burn constitutes the principal portion of the regeneration process. With the molecular oxygen level maintained below about 1.0 mole percent during this main burn, the burning of the coke consumes essentially all of the oxygen so that substantially no molecular oxygen is detected in the gaseous stream at the outlet of the reactor vessel. Near the end of the main burn, oxygen consumption across the catalyst bed will start to decrease producing a discernible concentration of molecular oxygen (about 0.2 mole percent) at the exit of the reactor. This point in the main burn is referred to as the oxygen breakthrough and essentially marks the end of the main burn. At this point the clean-up burn portion of the regeneration is initiated by gradually increasing the molecular oxygen concentration in the gas introduced to the catalyst bed while continuing to maintain the water partial pressure at no greater than about 1.0 psi. The oxygen concentration can usually be slowly increased to about 7.0 mole percent until the end of the clean-up burn which is indicated by a gradual decline in the water partial pressure and the temperature at the exit of the catalyst bed until the inlet and outlet temperatures of the catalyst bed merge at about 800°–830° F., i.e. there is essentially no temperature rise across the bed.

In general, the aromatic conversion catalysts regenerated in accordance with this invention are crystalline zeolites having a silica/alumina ratio greater than 12 and a Constraint Index (C.I.) between about 1 and about 12. The zeolites are generally termed ZSM-5 type zeolites.

The preferred class of zeolites defined herein are ZSM-5 type zeolites as exemplified by ZSM-5, ZSM-11, ZSM-12, ZSM-35, ZSM-38, with ZSM-5 being particularly preferred.

ZSM-5 is more particularly described in U.S. Pat. No. 3,702,886, the entire contents of which are incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The use of these zeolites as aromatic conversion catalysts are disclosed, for example, in the patent art discussed hereinbefore, such as U.S. Pat. Nos. 3,856,872, of Morrison; 3,856,873 of Burress; 4,163,028 of Tabak et al. and 4,236,996 of Tabak et al. The entire contents of these patents are incorporated herein by reference.

The regeneration of these aromatic conversion catalysts is disclosed in commonly assigned patent application Ser. No. 121,340, filed Feb. 14, 1980, the entire contents of which are incorporated herein by reference.

The following examples will serve to illustrate the subject invention.

EXAMPLE I

Four catalysts containing ZSM-5 zeolite were oxidatively regenerated under varying conditions. The effectiveness of the regeneration was evaluated in terms of the change in catalytic activity as measured by the "alpha value" ($\alpha$) of each catalyst.

The alpha value reflects the relative activity of a cataylst with respect to a high activity silica-alumina cracking catalyst. To determine the alpha value, as such term is used herein, n-hexane conversion is determined at about 800° F. Conversion is varied by variation in space velocity such that a conversion level of 10 to 60 percent of n-hexane is obtained and converted to a rate constant per unit volume of zeolite and compared with that of a silica-alumina catalyst which is normalized to a reference activity of 1000° F. Catalytic activity of the catalysts is expressed as a multiple of this standard, i.e. the silica-alumina standard. The silica-alumina reference catalyst contains about 10 weight percent $Al_2O_3$ and the remainder $SiO_2$. This method of determining alpha, modified as described above, is more fully described in the *Journal of Catalysis*, Vol. VI, pages 278–287, 1966.

Each of the catalysts evaluated was employed as a xylene isomerization catalyst before regeneration. Three of the regenerations were conducted with steamed H ZSM-5 catalysts and one with an unsteamed H ZSM-5 catalyst.

A description of the four catalysts and details of the regeneration of each is described below.

Sample No. 1

An unsteamed H ZSM-5 commercial catalyst having an initial alpha value of 200, before the xylene isomerization, was oxidativity regenerated at a water partial pressure of 1.1 psi. At the end of the regeneration, a sample of the catalyst showed an alpha value of 240.

Sample No. 2

A HZSM-5 catalyst, steamed in the laboratory to an initial alpha value of 92 was regenerated following xylene isomerization in the same fashion as Sample No. 1 except that the water partial pressure was 1.7 psi. A sample of the regenerated catalyst exhibited an alpha value of 68.

Sample Nos. 3 and 4

Two samples of a commercially steamed HZSM-5 catalyst having an initial alpha value of 100 were regenerated in the same fashion as Sample No. 1 except that the water partial pressure was 1.7 psi for Sample No. 3 while a water partial pressure of less than 0.1 psi was employed for Sample No. 4 through the use of gas driers. After the "wet" regeneration of Sample No. 3, the alpha value of the catalyst at the top and bottom of the bed was 37 and 39, respectively. Following the "dry" regeneration of Sample No. 4, the alpha value of the catalyst at the top of the bed was 70 while at the bottom of the bed it was 100. Some iron from the reactor was observed in the Sample No. 4 catalyst from the top of the bed which would appear to account for the lower alpha activity at the top of the bed. No loss in activity was observed for the bottom of the bed in the "dry" regeneration.

TABLE I

Table I, below, summarizes the results of these tests.

| Sample No. | Catalyst | Initial Alpha Activity (Before Isom Run) | $H_2O$ Partial Pressure during Regeneration, psi | Alpha Activity after regeneration | |
|---|---|---|---|---|---|
| | | | | top of bed | bottom of bed |
| 1 | Commercial Unsteamed H ZSM-5 | 200 | 1.1 | 240 | |
| 2 | Steamed H ZSM-5 | 92 | 1.7 | 68 | |
| 3 | Commercial Steamed H ZSM-5 | 100 | 1.7 | 37 | 39 |
| 4 | Commercial Steamed H ZSM-5 | 100 | <0.1 | 70 | 100 |

Sample No. 1 regenerated in accordance with the disclosure of application Ser. No. 121,340, shows that the activity of an unsteamed ZSM-5 zeolite catalyst can be enhanced by regeneration in the presence of steam at steam partial pressures below 4.0 psi. Sample Nos. 2 and 3 show that a presteamed ZSM-5 zeolite catalyst will lose activity by regeneration at water partial pressures above 1.0 psi while Sample No. 4 shows that the activity of a Sample No. 3 catalyst can be maintained by regeneration at water partial pressures below 1.0 psi.

Example II

The following example illustrates one embodiment of this invention. The catalyst being regenerated in accordance with this invention was ZSM-5 type zeolite catalyst prepared and utilized in a xylene isomerization process in accordance with the disclosure of U.S. Pat. No. 4,236,996, the entire contents of which are incorporated herein by reference. FIG. 1 is a flowplan illustrating the regeneration of this catalyst. Referring to FIG. 1, reactor 2 contained a fixed bed of about 18,000 pounds ZSM-5 type zeolite catalyst. The xylene isomerization run was terminated after a prolonged run for regeneration of the coked catalyst (approximately 55% coke on catalyst). The regeneration gas loop contained neither a recycle gas dryer nor the combination of a condenser and a gas - liquid separator, which are conventionally employed in many catalyst regeneration systems. The regeneration system consisted of compressor 4 and heater 6 plus piping connecting this equipment to the reactor.

Gas cooler 7 was provided to maintain the gaseous stream as it entered the compressor at a temperature below the design temperature of the compressor. Often, the hot gas leaving the reactor was at a temperature of about 850° F. whereas the maximum design inlet temperature to the compressor was about 620° F. Cooler 7 did not condense any water from the gaseous stream. Where the upper temperature limitation of the compressor is sufficiently high, this cooler may be eliminated. Provisions were made for bleeding recycle gas from the suction of the compressor and for the introduction of air and/or nitrogen into the suction of the compressor. The location of the air and nitrogen lines is not critical so long as they are downstream from where the gas is removed from the circulating stream. Thus, where desired, the air and nitrogen lines could be located in the discharge from the compressor.

Figure 2:
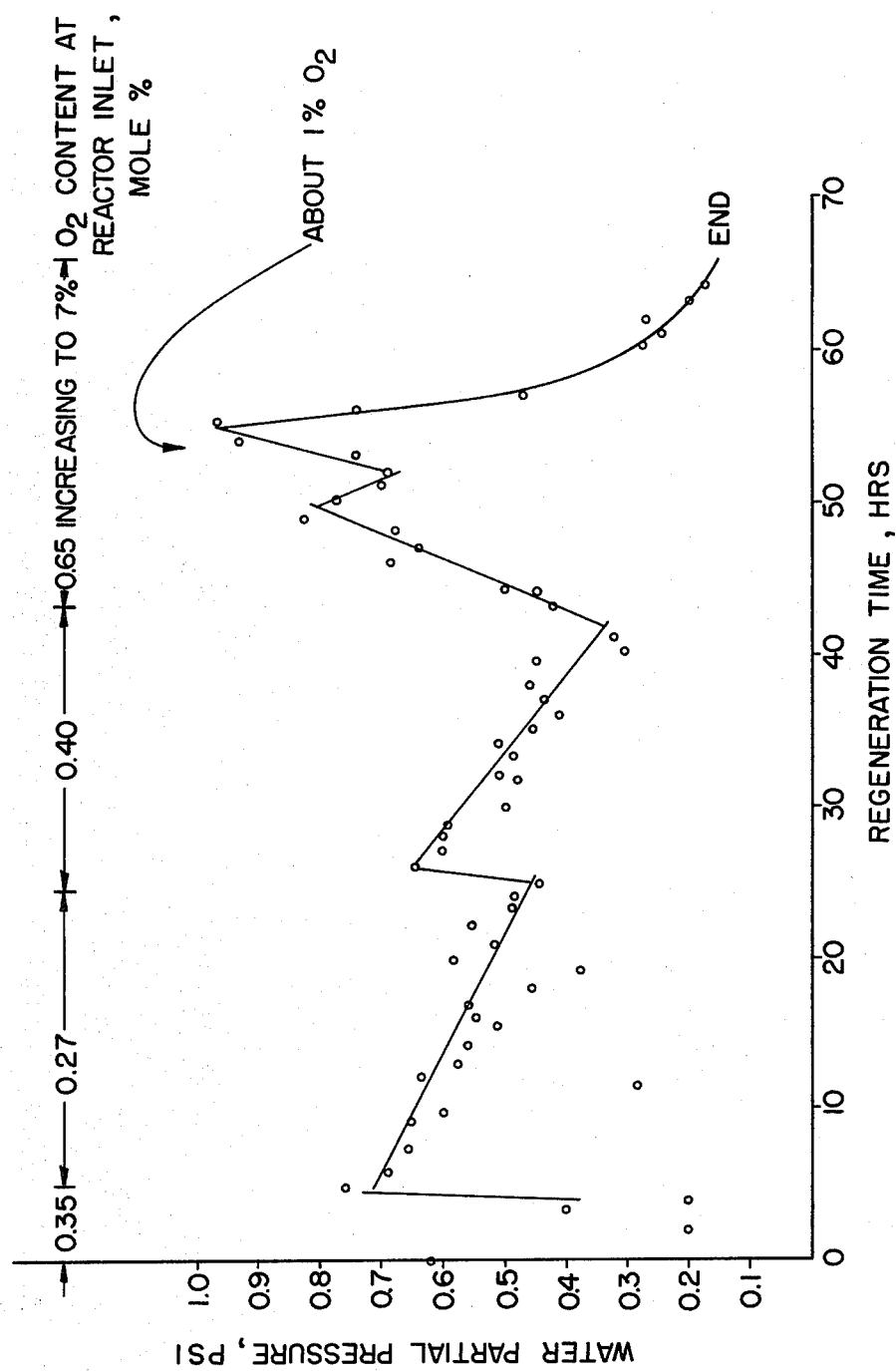
FIG. 2 is a graph of the water partial pressure versus time during a regeneration conducted in accordance with the subject invention.

The regeneration of the catalyst was initiated by supplying dry air(−58° dew point) through line 8 and dry nitrogen (−60° F. dew point) through line 10 into line 20 to provide a regeneration gas having an oxygen content of about 0.35 mole percent and a water partial pressure of about 0.6 psi. Compressor 4 circulated about 40,000 m³/hr. of this gas through line 12 and through heater 6 to provide a heated oxygen containing gas to initiate the regeneration. Reactor pressure during the regeneration averaged about 48 psia. Hot gas flowed from heater 6 through line 14 into the bed of coked catalyst in reactor 2. The heat provided by heater 6 was slowly increased until burning was initiated at a temperature of 720° F. at the inlet to the catalyst bed. Hot gas exited the reactor and flowed through line 16, gas cooler 7 and line 20 to the compressor. Hot moist gas was removed from line 16 through line 18. This removal through line 18 was coordinated with the addition into line 20 of dry air and dry nitrogen through lines 8 and 10, respectively, to maintain an oxygen content at 0.35 mole percent, and a water partial pressure at about 0.6 psi in the circulating regeneration gas at the inlet to reactor 2. Near the end of the first five hours of the regeneration cycle, the water partial pressure in the circulating gas recycle stream was increasing rapidly so that the oxygen content was reduced to 0.27 mole percent to maintain the water partial pressure below 1.0 psi. The levels of water partial pressure and oxygen content during the regeneration are presented graphically in FIG. 2. This reduced oxygen content necessitated an increase in the temperature of the recirculating gas from heater 6 to about 743° F. to maintain the burning of the coke in the bed of catalyst. The oxygen level of 0.27 mole percent was maintained for about 20 hours at which time the water partial pressure had decreased sufficiently to permit an adjustment in the air-nitrogen additions to raise the oxygen content to 0.4 mole percent. Although the water partial pressure in the recycle gas immediately increased at this oxygen level, it was not excessive and gradually declined while the oxygen level was maintained at 0.4 mole percent. After 43 hours into the regeneration, oxygen breakthrough occurred, i.e., oxygen was detected in the gases exiting from reactor 2. The air rate was then increased to raise the oxygen level to 0.65 mole percent which resulted in a gradual increase in the water partial pressure until at about the 50 hour level the water partial pressure started to decline. At this point the oxygen level was gradually increased. After oxygen breakthrough occurred again, it took 19 additional hours to burn off the balance of the coke. During this clean-up phase, the oxygen level was gradually increased until it reached about 7 mole percent at the end of the regeneration. The inlet temperature of the bed was at about 748° F. during this period. As the water partial pressure decreased so did the outlet temperature. The inlet temperature was therefore gradually increased until the inlet and outlet temperature finally merged at 815° F. at the end of the regeneration.

Upon return of the unit to xylene isomerization, it was found that the catalyst regeneration had been effective to the point that the operating conditions and the overall results were essentially the same as those experienced for the same period in the previous operating cycle.

What is claimed is:

1. In a process for the conversion of an aromatic containing feedstock in which said feedstock is contacted in a reactor vessel, under conversion conditions, with a catalyst comprising a ZSM-5 type zeolite having a silica to alumina mole ratio of at least 12 and a constraint index within the approximate range of 1 to 12, and which includes a regeneration step to burn off carbonaceous materials which deposit on said catalyst, said regeneration step comprising contacting said catalyst containing carbonaceous materials with a continuous closed loop flow of a gas stream comprising oxidizing gas and steam at regeneration conditions including a steam partial pressure of between about 0.1 psi and about 4.0 psi, a contact time of between about 12 hours and about 72 hours and a temperature of between about 700° F. and about 1000° F. the improvement which comprises:

(a) removing from said continuous closed loop flow a portion of said gas stream, and (b) introducing into said continuous closed loop flow a quantity of a low moisture content, molecular-oxygen containing gas, said portion and said quantity being effective, collectively, to maintain, in the closed loop flow at the inlet to said reactor vessel, a molecular oxygen content no greater than about 1.0 mole percent and a water partial pressure no greater than about 1.0 psi.

2. A process according to claim 1 wherein the molecular-oxygen containing gas comprises air.

3. A process according to claim 1 wherein the molecular-oxygen containing gas comprises oxygen and an inert gas.

4. A process according to claim 3 wherein the inert gas comprises nitrogen.

5. A process according to claim 1 wherein the molecular-oxygen containing gas is a mixture of air and nitrogen.

6. A process according to claim 1 wherein the low moisture content molecular oxygen containing gas has a dew point of less than about −15° F.

7. A process according to claim 1 including the following additional step:

(c) following the breakthrough of oxygen in the gas stream leaving said reactor vessel, increasing the molecular oxygen content at the inlet to said reactor vessel above about 1.0 mole percent while maintaining the water partial pressure at no greater than about 1.0 psi until there is essentially no temperature difference across the catalyst bed.

8. A process according to claim 1 wherein the zeolite is ZSM-5, ZSM-11, ZSM-12, ZSM-35 or ZSM-38.

9. A process according to claim 1 wherein the zeolite is ZSM-5.

10. A process according to claim 1 wherein the feedstock is a mixture of eight carbon atom aromatic hydrocarbon compounds comprising xylene and ethylbenzene and the conversion is xylene isomerization.

11. A process according to claim 10 wherein the zeolite has been steamed under conditions of temperature, pressure and time such that the steamed zeolite requires an increased isomerization reaction temperature of at least 50° F. to equal the ethylbenzene conversion by the unsteamed zeolite.

12. In a process for isomerizing the xylene content of a charge mixture of eight carbon atom aromatic hydrocarbon compounds which mixture contains xylene and ethylbenzene by contact at conversion conditions including a temperature of about 700° to about 1000° F. with a catalyst comprising a ZSM-5 type zeolite having a silica/alumina ratio greater than 12 and a constraint index of 1 to 12, said zeolite having been steamed prior to said contact under temperature and pressure conditions and a period of time such that the steamed zeolite requires an increased reaction temperature of at least 50° F. to equal the ethylbenzene conversion by the unsteamed zeolite and regenerating said catalyst to burn off carbonaceous materials which deposit on said catalyst by contacting said catalyst containing carbonaceous materials with a continuous closed loop flow of a gas stream comprising molecular-oxygen containing gas under regeneration conditions comprising a water partial pressure of between about 0.1 and about 1.0 psi, a contact time of between about 12 and about 120 hours and a temperature of between about 700° and about 925° F., the improvement in the regeneration which comprises:

(a) removing from said continuous closed loop flow a portion of said gas stream, and (b) introducing into said continuous closed loop flow a quantity of a low moisture content, molecular-oxygen containing gas, said portion and said quantity being effective, collectively, to maintain, in the closed loop flow at the inlet to said reactor vessel, a molecular oxygen content no greater than about 1.0 mole percent and a water partial pressure no greater than about 1.0 psi.

13. A process according to claim 12 wherein the molecular-oxygen containing gas comprises air.

14. A process according to claim 12 wherein the molecular-oxygen containing gas comprises oxygen and an inert gas.

15. A process according to claim 14 wherein the inert gas comprises nitrogen.

16. A process according to claim 12 wherein the molecular-oxygen containing gas is a mixture of air and nitrogen.

17. A process according to claim 12 wherein the low moisture content molecular oxygen containing gas has a dew point of less than about $-15°$ F.

18. A process according to claim 12 including the following additional step:

(c) following the breakthrough of oxygen in the gas stream leaving said reactor vessel, increasing the molecular oxygen content at the inlet to said reactor vessel above about 1.0 mole percent while maintaining the water partial pressure at no greater than about 1.0 psi until there is essentially no temperature difference across the catalyst bed.

19. A process according to claim 12 wherein the zeolite is ZSM-5, ZSM-11, ZSM-12, ZSM-35 or ZSM-38.

20. A process according to claim 12 wherein the zeolite is ZSM-5.

* * * * *